(12) United States Patent
Wada

(10) Patent No.: US 10,098,791 B2
(45) Date of Patent: Oct. 16, 2018

(54) CRUSHER, ABSORBER-MANUFACTURING DEVICE, AND PULP SHEET-CRUSHING METHOD

(71) Applicant: ZUIKO CORPORATION, Osaka (JP)

(72) Inventor: Takao Wada, Osaka (JP)

(73) Assignee: ZUIKO CORPORATION, Settsu-Shi, Osaka (JP)

( * ) Notice: Subject to any disclaimer, the term of this patent is extended or adjusted under 35 U.S.C. 154(b) by 211 days.

(21) Appl. No.: 14/917,616

(22) PCT Filed: Sep. 9, 2014

(86) PCT No.: PCT/JP2014/073771
§ 371 (c)(1),
(2) Date: Mar. 9, 2016

(87) PCT Pub. No.: WO2015/045848
PCT Pub. Date: Apr. 2, 2015

(65) Prior Publication Data
US 2016/0206480 A1     Jul. 21, 2016

(30) Foreign Application Priority Data

Sep. 26, 2013  (JP) .................................. 2013-199347

(51) Int. Cl.
*A61F 13/00*     (2006.01)
*A61F 13/15*     (2006.01)
(Continued)

(52) U.S. Cl.
CPC .. *A61F 13/15617* (2013.01); *A61F 13/15723* (2013.01); *A61F 13/15747* (2013.01);
(Continued)

(58) Field of Classification Search
CPC .......... A61F 13/15617; A61F 13/15723; A61F 13/15747; B02C 18/22; D21B 1/066; D21B 1/068
See application file for complete search history.

(56) References Cited

U.S. PATENT DOCUMENTS 3,606,175 A    9/1971  Appel
4,241,881 A   12/1980  Laumer
(Continued)

FOREIGN PATENT DOCUMENTS

CN    101177004    5/2008
CN    102665630    9/2012
(Continued)

OTHER PUBLICATIONS

European Search Report dated Sep. 2, 2016.
(Continued)

*Primary Examiner* — Timothy Kennedy
(74) *Attorney, Agent, or Firm* — Gerald E. Hespos; Michael J. Porco; Matthew T. Hespos

(57) ABSTRACT

Provided is a crusher capable of omitting a device for feeding a pulp sheet from outside into inside of a casing or suppressing a driving force of this device to be small and an absorber-manufacturing device provided with the same. A pulp sheet (P) is guided to a contact position (m) where the pulp sheet (P) and crushing edges (9b) of a cutter (9) come into contact from a position upstream of a virtual line (L3) orthogonal to a tangent line (L2) of a rotational path (R1) of the crushing edges (9b) at the contact position (m) and passing through the contact position (m) in a rotational direction (Y2) by a guiding section (5a) provided in a casing (5) and configured to guide the pulp sheet (P) from outside into inside of the casing (5).

6 Claims, 3 Drawing Sheets

(51) Int. Cl.
  *B02C 18/22* (2006.01)
  *D21B 1/06* (2006.01)
(52) U.S. Cl.
  CPC .............. *B02C 18/22* (2013.01); *D21B 1/061* (2013.01); *D21B 1/066* (2013.01); *B02C 2018/2208* (2013.01)

(56) References Cited

U.S. PATENT DOCUMENTS

| | | | |
|---|---|---|---|
| 4,673,136 A * | 6/1987 | Bianco | D21B 1/066 241/28 |
| 2005/0150986 A1 | 7/2005 | Castronovo | |
| 2012/0280434 A1 | 11/2012 | Hoshika et al. | |
| 2013/0014899 A1 | 1/2013 | Nakano | |

FOREIGN PATENT DOCUMENTS

| | | |
|---|---|---|
| CN | 102724940 | 10/2012 |
| DE | 113079 C | 6/1899 |
| JP | S51149905 A | 12/1976 |
| JP | S52066774 A | 6/1977 |
| JP | 56-101961 | 8/1981 |
| JP | 11-5217 | 1/1999 |
| JP | 2008-29928 | 2/2008 |
| JP | 2009114555 A | 5/2009 |
| JP | 2011-152351 | 8/2011 |
| WO | 2006/078679 | 7/2006 |

OTHER PUBLICATIONS

International Search Report, dated Dec. 4, 2014.
Opinion of Appealer, Dec. 28, 2015.
Japanese Office Action and English Translation dated Jun. 6, 2017.

* cited by examiner

CRUSHER, ABSORBER-MANUFACTURING DEVICE, AND PULP SHEET-CRUSHING METHOD

TECHNICAL FIELD

The present invention relates to a crusher for crushing a pulp sheet, an absorber-manufacturing device provided with the same, and a pulp sheet-crushing method for crushing a pulp sheet using the crusher.

BACKGROUND ART

An absorber used in a disposable diaper or the like is manufactured by molding pulp fibers obtained by crushing a pulp sheet into a predetermined shape.

For example, a crusher described in Japanese Unexamined Patent Publication No. 2011-152351 is known as a device for crushing a pulp sheet.

The crusher described in Japanese Unexamined Patent Publication No. 2011-152351 includes a cutter which rotates about a predetermined axis and has crushing edges configured to come into contact with a pulp sheet on the outer periphery, and a casing which houses the cutter.

A feeding port for guiding the pulp sheet into the inside of the casing, in which the cutter is housed, from the outside of the casing is open on the casing.

However, the feeding port of Japanese Unexamined Patent Publication No. 2011-152351 is shaped along a straight line extending in a radial direction of the cutter through a rotation center of the cutter, i.e. shaped along a straight line orthogonal to a tangent line to a rotational path of the crushing edges.

Thus, in the device of Japanese Unexamined Patent Publication No. 2011-152351, the pulp sheet is fed into the inside of the casing from the outside of the casing in a posture in which the pulp sheet extends in the direction orthogonal to the tangent line to the rotational path of the crushing edges at a feeding position.

Here, a rotational force of the cutter is generated in a tangential direction to the rotational path of the crushing edges.

Accordingly, in the device of Japanese Unexamined Patent Publication No. 2011-152351, a force of a direction to feed the pulp sheet into the inside of the casing is not applied to the pulp sheet from the cutter. Thus, a separate device for feeding the pulp sheet into the inside of the casing from the outside of the casing has to be provided or a driving force of the device for feeding the pulp sheet has to be increased. Further, the pulp sheet fed into the inside of the casing by this device may collide with the cutter and be bounced back toward the outside of the casing and clogging may occur at the feeding port.

SUMMARY OF INVENTION

The present invention aims to provide a crusher capable of omitting a device for feeding a pulp sheet into the inside of a casing from the outside of the casing or suppressing a driving force of this device to be small and suppressing the clogging of the pulp sheet, an absorber-manufacturing device provided with the same and a pulp sheet-crushing method.

To solve the above problem, the present invention provides a crusher for crushing a pulp sheet with a cutter configured to rotate about a predetermined axis and a casing configured to house the cutter, the cutter having, on an outer periphery thereof, a crushing edge configured to crush the pulp sheet by coming into contact with the pulp sheet, the casing including a guiding section configured to guide the pulp sheet toward a contact position, where the pulp sheet and the crushing edge of the cutter come into contact, from outside of the casing into inside of the casing, and the guiding section guiding the pulp sheet toward the contact position from a position upstream of a virtual line orthogonal to a tangent line to a rotational path of the crushing edge at the contact position and passing through the contact position in a rotational direction.

Further, the present invention provides an absorber-manufacturing device for manufacturing an absorber with the above crusher, a fiber stacking machine configured to mold pulp fibers crushed by the crusher into a predetermined shape of the absorber, and a duct configured to introduce the pulp fibers from the crusher to the fiber stacking machine.

Further, the present invention provides a pulp sheet-crushing method for crushing a pulp sheet using a crusher with a cutter configured to rotate about a predetermined axis and a casing configured to house the cutter, a crushing edge configured to crush the pulp sheet by coming into contact with the pulp sheet being provided on an outer periphery of the cutter having and a guiding section configured to guide the pulp sheet toward a contact position, where the pulp sheet and the crushing edge of the cutter come into contact, from outside of the casing into inside of the casing being provided in the casing, the pulp sheet-crushing method including a step of supplying the pulp sheet into the crusher through the guiding section such that the pulp sheet moves toward the contact position from a position upstream of a virtual line orthogonal to a tangent line to a rotational path of the crushing edge at the contact position and passing through the contact position in a rotational direction.

According to the present invention, it is possible to omit a device for feeding a pulp sheet into the inside of a casing from the outside of the casing or suppress a driving force of this device to be small and the clogging of the pulp sheet is suppressed.

DESCRIPTION OF EMBODIMENT

Hereinafter, an embodiment of the present invention is described with reference to the accompanying drawings. Note that the following embodiment is a specific example of the present invention and not of the nature to limit the technical scope of the present invention.

Figure 1:
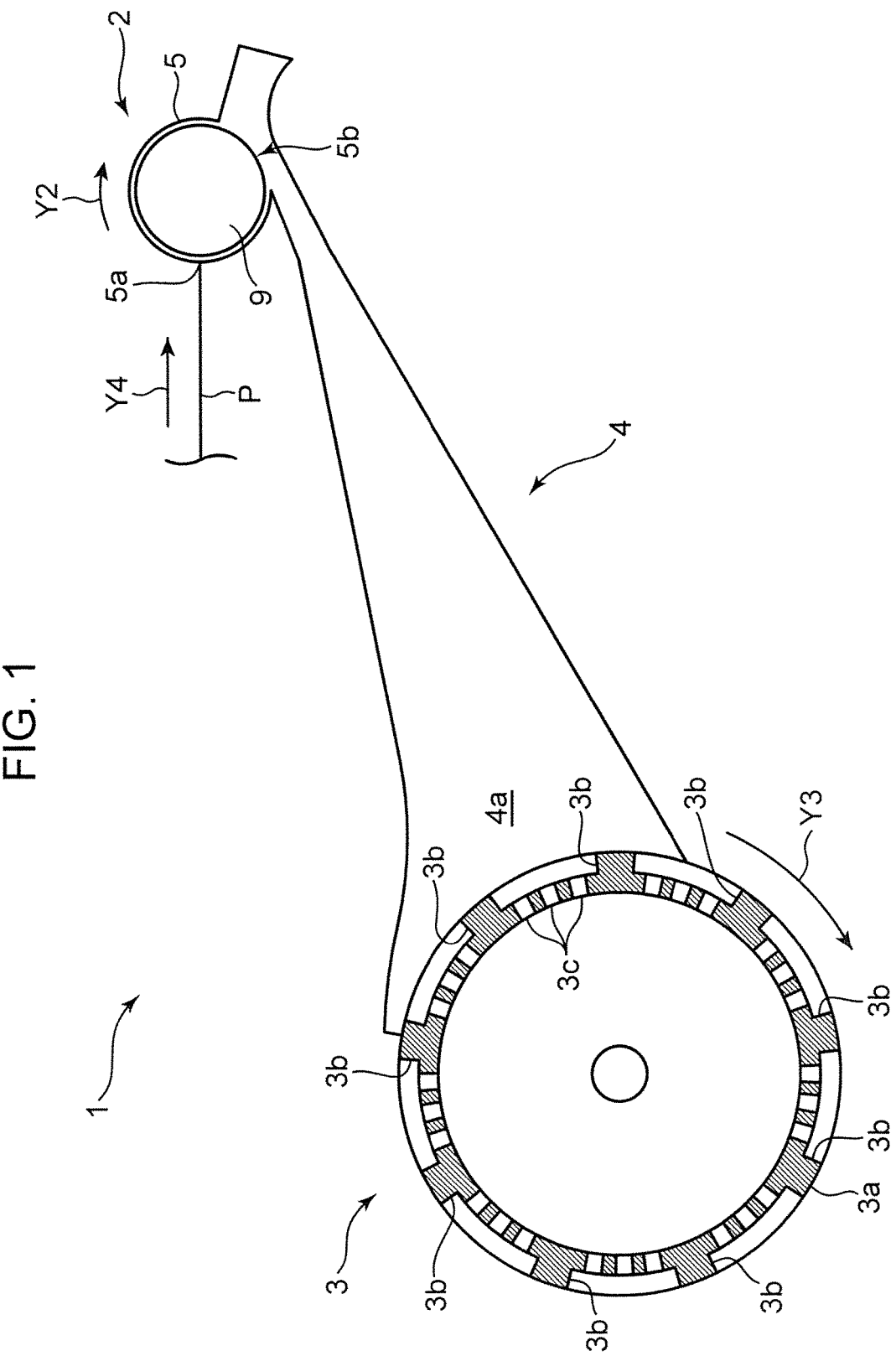
FIG. 1 is a schematic side view showing an overall configuration of an absorber-manufacturing device according to the present invention.

With reference to FIG. 1, an absorber-manufacturing device 1 includes a crusher 2 for producing pulp fibers by crushing a pulp sheet P, a fiber stacking machine 3 for molding the pulp fibers crushed by the crusher 2 into a predetermined shape as the shape of an absorber, and a duct 4 for introducing the pulp fibers from the crusher 2 to the fiber stacking machine 3.

The duct 4 is connected to a later-described outlet port 5b for pulp fibers in the crusher 2.

The fiber stacking machine 3 includes a rotary drum 3a formed with recesses 3b, which are shaped to correspond to the shape of the absorber, on the outer peripheral surface thereof The rotary drum 3a is so arranged that a part of the outer peripheral surface thereof is located in a downstream opening 4a of the duct 4, and rotatable in a direction of an arrow Y3 to successively locate the recesses 3b in the opening 4a.

Further, the rotary drum 3a is provided with suction ports 3c communicating with bottom parts of the recesses 3b. By sucking air in the recesses 3b via the suction ports 3c, the pulp fibers in the duct 4 are sucked into the recesses 3b to be molded.

Hereinafter, a specific configuration of the crusher 2 is described with reference to FIGS. 1 and 2.

The crusher 2 includes a cutter 9, a cylindrical rotary shaft 8, a casing 5 for housing the cutter 9 and a motor 7 for rotationally driving the cutter 9.

The rotary shaft 8 is fixed to the cutter 9 while penetrating through the cutter 9 in a thickness direction. The cutter 9 rotates about a center axis O of this rotary shaft 8. In an example shown in FIG. 2, the cutter 9 rotates clockwise as indicated by an arrow Y2. The cutter 9 includes a cylindrical main body part 9a fixed to the rotary shaft 8 and centered on the center axis O of the rotary shaft 8 and a plurality of crushing edges 9b. The respective crushing edges 9b project radially outwardly of the rotary shaft 8 from the main body part 9a and are arranged side by side in a circumferential direction of the rotary shaft 8. In this embodiment, the rotary shaft 8 extends in a horizontal direction and the cutter 9 rotates about the axis O extending in the horizontal direction. Further, a cross-section of the main body part 9a of the cutter 9 along a plane orthogonal to the rotary shaft 8, i.e. extending in a vertical direction is circular. Note that the horizontal direction mentioned here means not only a perfectly horizontal direction, but also a direction slightly inclined with respect to the horizontal direction.

The casing 5 includes an inlet port (guiding section) 5a for guiding the pulp sheet P into the inside of the casing 5 from the outside of the casing 5. Specifically, the casing 5 includes a peripheral wall 5c covering the outer periphery of the cutter 9. The inlet port 5a is a through hole formed on this peripheral wall 5c and penetrating through the peripheral wall 5c. A hole height of the inlet port 5a in a vertical direction is set at a value slightly larger than a thickness of the pulp sheet P. Note that the pulp sheet P has a predetermined width in a direction perpendicular to the plane of FIG. 2 and the inlet port 5a extends along the width of the pulp sheet P.

The pulp sheet P is guided into the inside of the casing 5 toward a contact position m where the pulp sheet P comes into contact with the crushing edges 9b of the cutter 9. The pulp sheet P guided to the contact position m is crushed by the crushing edges 9b of the rotating cutter 9.

The casing 5 further includes the outlet port 5b for guiding pulp fibers crushed by the crushing edges 9b to the outside of the casing 5. The inlet port 5a and the outlet port 5b are provided at positions different in a rotational direction of the cutter 9.

The pulp fibers produced by crushing the pulp sheet P by the crushing edges 9b at the contact position m move toward a downstream side in the rotational direction Y1 of the cutter 9 according to the rotation of the cutter 9 and led out to the outside of the casing 5 from the outlet port 5b. The pulp fibers led out from the outlet port 5b are introduced to the fiber stacking machine 3 by the duct 4.

The inlet port 5a of the casing 5 is described in detail.

Figure 2:
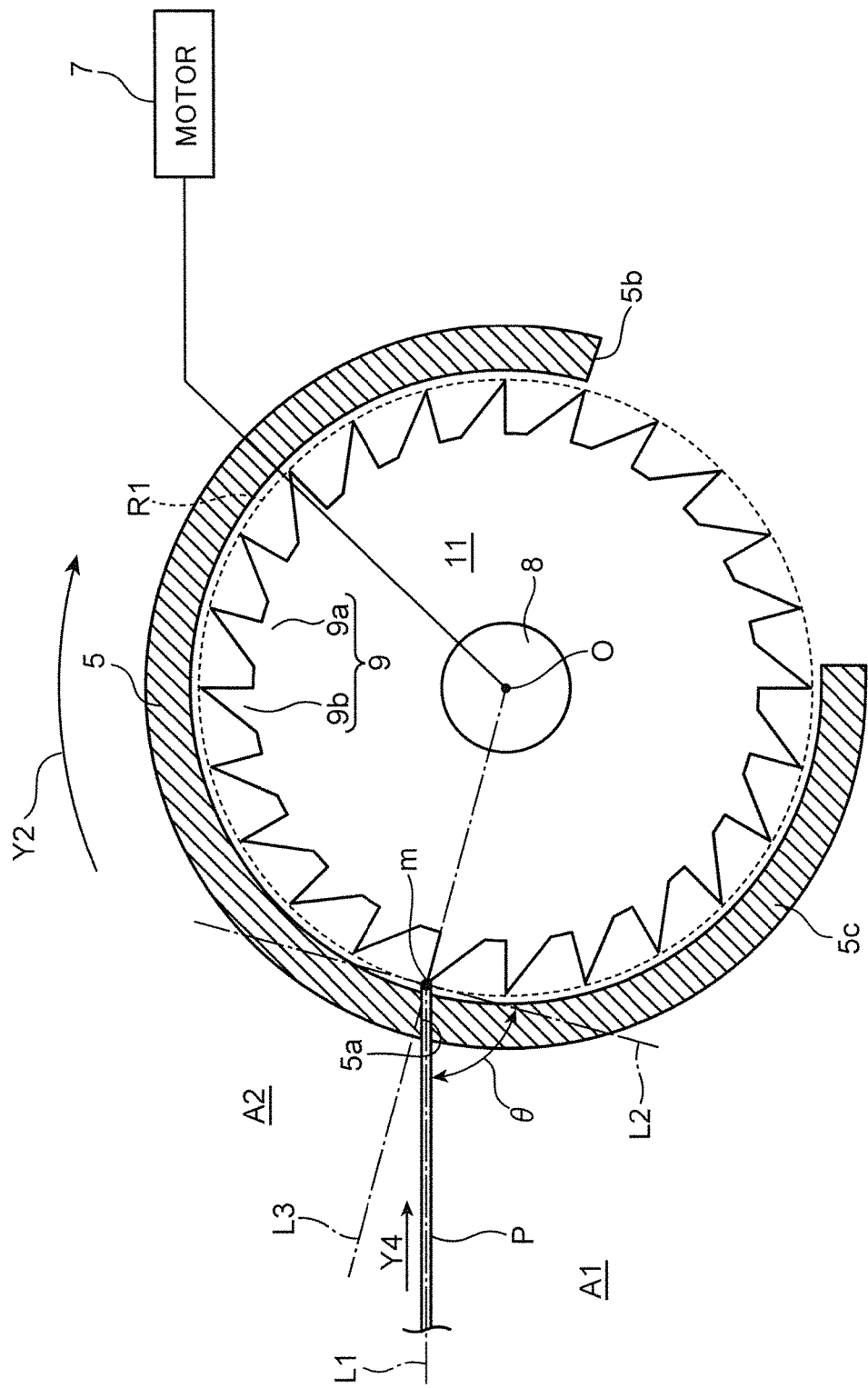
FIG. 2 is a side view in section enlargedly showing a crusher shown in FIG. 1.

The inlet port 5a extends along a straight line L1 shown in FIG. 2.

The straight line L1 extends from a position upstream of a vertical line L3 in the rotational direction Y2 toward the contact position m in a cross-section perpendicular to the rotary shaft 8. The virtual line L3 is a line orthogonally intersecting with a tangent line L2 to a rotational path R1 of the crushing edges 9b at the contact position m and passing through the contact position m. Here, in FIG. 2, the position upstream of the virtual line L3 in the rotational direction Y2 is a position in an area indicated by A1. Specifically, an area upstream of the virtual line L3 in the rotational direction Y2 is an area upstream of the virtual line L3 in the rotational direction Y2 out of an area more outward than the tangent line L2 in a radial direction of the cutter 9 (sum area of A1 and A2).

Note that, in this embodiment, the cross-section of the main body part 9a of the cutter 9 along the plane orthogonal to the rotary shaft 8 is circular as described above. Thus, the rotational path R1 of the crushing edges 9b projecting radially outwardly of the rotary shaft 8 from this main body part 9a is circular in a cross-section perpendicular to the rotary shaft 8. The virtual line L3 passes through the rotation center O of the cutter 9.

The pulp sheet P is guided to the contact position m along the straight line L1 by the inlet port 5a. Specifically, the pulp sheet P is guided toward the contact position m from the position upstream of the virtual line L3 orthogonal to the tangent line L2 to the rotational path R1 of the crushing edges 9b at the contact position m and passing through the contact position m in the rotational direction.

The straight line L1 is inclined with respect to the tangent line L2. Associated with this, the pulp sheet P is guided to the contact position m in a posture inclined with respect to the tangent line L2 by the inlet port 5a. In this embodiment, an angle of inclination θ between the straight line L1 and the tangent line L2 of the inlet port 5a is set at about 75°. This angle of inclination θ is preferably, for example, 70 to 80°.

The inlet port 5a is so provided that the contact position m is located higher than a vertical center of the cutter 9. In this embodiment, the inlet port 5a horizontally extends at a position higher than the vertical center of the cutter 9. Associated with this, the contact position m is located at the same height position as the inlet port 5a and higher than the vertical center of the cutter 9. Further, as the inlet port 5a horizontally extends, the pulp sheet P is guided in the horizontal direction by the inlet port 5a.

As just described, in this embodiment, the inlet port 5a is shaped to be able to guide the pulp sheet P toward the contact position m from the position upstream of the virtual line L3 orthogonal to the tangent line L2 to the rotational path R1 of the crushing edges 9b at the contact position m and passing through the contact position m in the rotational direction. Further, the inlet port 5a is shaped to be able to guide the pulp sheet P to the contact position m in the posture inclined with respect to the tangent line L2 (tangent line L2 to the rotational path R1 of the crushing edges 9b at the contact position m). Furthermore, the inlet port 5a is shaped to be able to guide the pulp sheet P in the horizontal direction.

As described above, by the inlet port 5a, the pulp sheet P is guided toward the contact position m from the position upstream of the virtual line L3 orthogonal to the tangent line L2 to the rotational path R1 of the crushing edges 9b at the contact position m and passing through the contact position m in the rotational direction.

Specifically, the pulp sheet P is crushed by performing a step of supplying the pulp sheet P to the crusher 2 through the inlet port 5a such that the pulp sheet P moves toward the contact position m from the position upstream of the virtual line L3 orthogonal to the tangent line L2 to the rotational path R1 of the crushing edges 9b at the contact position m and passing through the contact position m in the rotational direction.

Thus, a part of a rotational force of the cutter 9 generated toward a downstream side in the rotational direction Y2 along the tangent line L2 to the rotational path R1 of the crushing edges 9b can be caused to act on the pulp sheet P as a force for pulling the pulp sheet P into the inside of the casing 5 from the outside of the casing 5.

Figure 3:
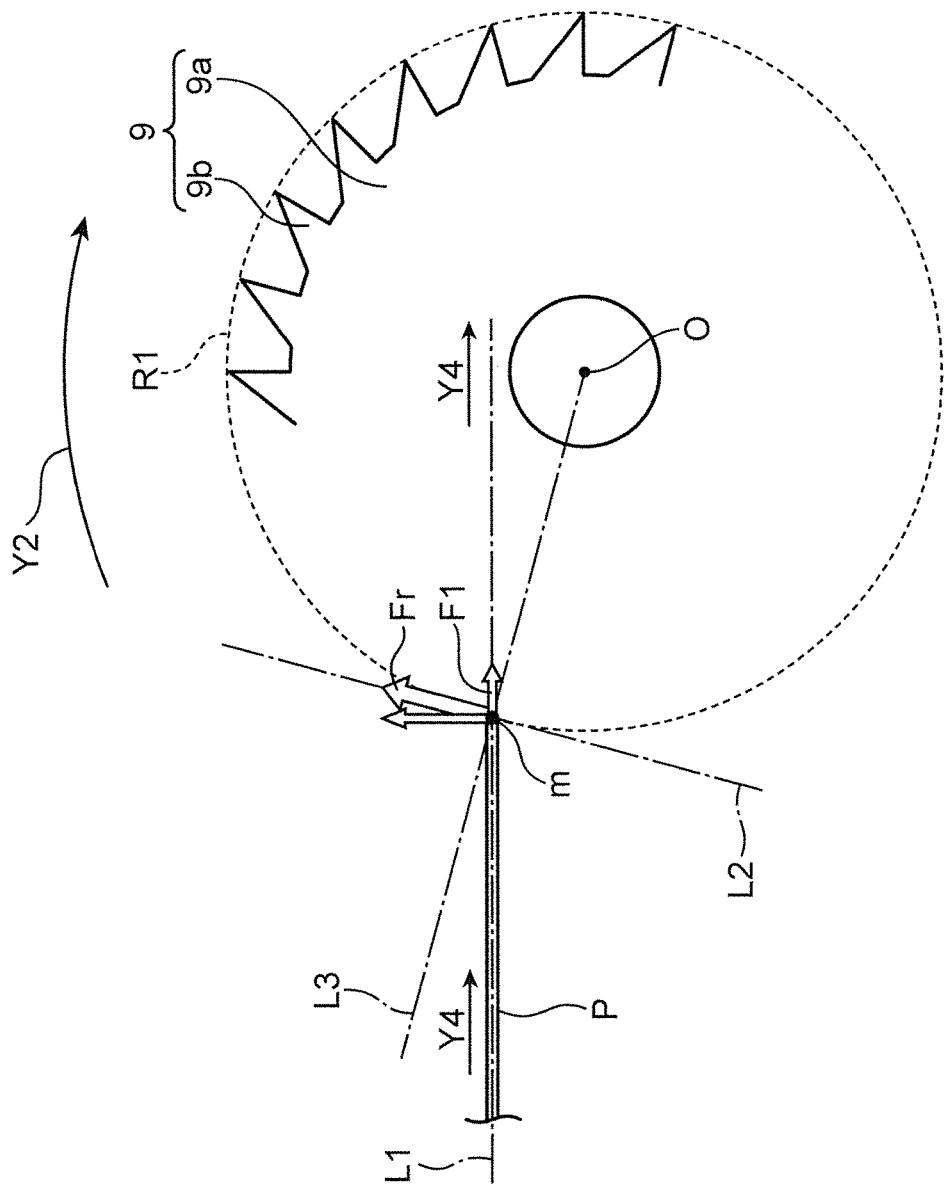
FIG. 3 is a diagram showing an action of a rotational force of a cutter on a pulp sheet.

The force that acts on the pulp sheet P is specifically described using FIG. 3. FIG. 3 is a diagram in which parts of FIG. 2 are omitted.

The rotational force of the cutter 9 is generated toward the downstream side in the rotational direction Y2 of the cutter 9 along the tangent line L2 to the rotational path R1 of the crushing edges 9b at the contact position m as indicated by an arrow Fr.

Here, for example, if the pulp sheet P is guided to the contact position m along the virtual line L3 orthogonal to the tangent line L2, a direction of action of the rotational force Fr of the cutter 9 and a direction in which the pulp sheet P is guided, i.e. a moving direction of the pulp sheet P in the casing 5 are orthogonal. Thus, the force in the moving direction is not applied to the pulp sheet P from the cutter 9. Therefore, the pulp sheet P cannot be pulled into the inside from the outside of the casing 5 by the rotational force Fr of the cutter 9.

Contrary to this, in the crusher 2 according to this embodiment, the pulp sheet P is guided toward the contact position m from the position upstream of the virtual line L3 orthogonal to the tangent line L2 in the rotational direction Y2 of the cutter 9 as described above. Specifically, a moving direction of the pulp sheet P from the outside into the inside of the casing 5 indicated by an arrow Y4 is not orthogonal to the direction of action of the rotational force Fr of the cutter 9. Further, the rotational force Fr acts toward the downstream side in the rotational direction, whereas the moving direction of the pulp sheet P from the outside into the inside of the casing 5 is a direction moving from the upstream side toward the downstream side in the rotational direction and the same direction as the direction of action of the rotational force Fr in the rotational direction.

Thus, a component F1 in the moving direction shown by the arrow Y4 out of the rotational force Fr of the cutter 9 acts on the pulp sheet P. Upon receiving this force Fl, the pulp sheet P is pulled into the inside of the casing 5.

Thus, according to the present invention, the pulp sheet P can be reliably pulled into the inside of the casing 5 from the outside of the casing 5 without separately providing a device for feeding the pulp sheet P from the outside of the casing 5 into the inside of the casing 5 or while a driving force of this device is suppressed to be small. Further, the bounceback of the pulp sheet P toward the outside of the casing 5 at the time of contact with the cutter 9 is suppressed. Thus, the clogging of the pulp sheet P near the inlet port 5a is suppressed.

Further, according to the above embodiment, the following effects are exhibited.

Since the inlet port 5a guides the pulp sheet P to the contact position m in the posture inclined with respect to the tangent line L2 to the rotational path R1 of the crushing edges 9b at the contact position m, a part of the rotational force Fr of the cutter 9 can be caused to act on the pulp sheet P as a force for moving the pulp sheet P toward the cutter 9. Thus, the pulp sheet P can be pulled toward the cutter 9 and reliably crushed by the cutter 9.

Since the rotary shaft 8 of the cutter 9 horizontally extends and the contact position m is located higher than the vertical center of the cutter 9, it can be avoided that the pulp fibers produced by crushing the pulp sheet P fall down below the cutter 9 by their own weights. This makes it more reliable to convey the pulp fibers toward the downstream side in the rotational direction of the cutter 9 according to the rotation of the cutter 9.

Since the inlet port 5a guides the pulp sheet P in the horizontal direction, it can be avoided that the own weight of the pulp sheet P affects a moving speed of the pulp sheet P from the outside into the inside of the casing 5. Thus, the moving speed of the pulp sheet P can be determined by the rotational force of the cutter 9 or the driving force of the separately provided device for feeding the pulp sheet P from the outside into the inside of the casing 5. This facilitates the management of the moving speed of the pulp sheet P.

Note that the following embodiments can be also adopted after the inlet port is configured to guide the pulp sheet P toward the contact position m from the position upstream of the virtual line L3 orthogonal to the tangent line L2 to the rotational path R1 of the crushing edges 9b at the contact position m and passing through the contact position m in the rotational direction.

The inlet port 5a may guide the pulp sheet P to the contact position m along the tangent line L2 to the rotational path R1 of the crushing edges at the contact position m.

The contact position m may be located lower than the vertical center of the cutter 9.

The inlet port 5a may guide the pulp sheet P to the contact position m in a posture inclined with respect to the horizontal direction.

The center axis O of the rotary shaft 8 serving as a center of rotation of the cutter 9 may not horizontally extend.

Note that the aforementioned specific embodiment mainly includes inventions having the following configurations.

Specifically, the present invention provides a crusher for crushing a pulp sheet, the crusher including a cutter configured to rotate about a predetermined axis and a casing configured to house the cutter, the cutter having, on an outer periphery thereof, a crushing edge configured to crush the pulp sheet by coming into contact with the pulp sheet, the casing including a guiding section configured to guide the pulp sheet toward a contact position, where the pulp sheet and the crushing edge of the cutter come into contact, from outside of the casing into inside of the casing, and the guiding section guiding the pulp sheet toward the contact position from a position upstream of a virtual line orthogonal to a tangent line to a rotational path of the crushing edge at the contact position and passing through the contact position in a rotational direction.

According to the present invention, since the guiding section guides the pulp sheet toward the contact position from the position upstream of the virtual line orthogonal to the tangent line to the rotational path of the crushing edge at the contact position and passing through the contact position in the rotational direction, a part of a rotational force of the cutter generated toward a downstream side in the rotational direction of the cutter along the tangential direction to the rotational path of the crushing edge can be caused to act on the pulp sheet as a force for pulling the pulp sheet from the outside of the casing into the inside of the casing.

Thus, according to the present invention, the pulp sheet can be pulled into the inside of the casing from the outside of the casing by the rotational force of the cutter and a device for feeding the pulp sheet can be omitted or a driving force of this device can be suppressed to be small. Further, since the pulp sheet is smoothly pulled into the inside of the casing by the rotational force of the cutter, the bounce-back of the pulp sheet toward the outside of the casing can be suppressed. This suppresses the clogging of the pulp sheet at the guiding section.

In the above crusher, the guiding section preferably guides the pulp sheet to the contact position in a posture inclined with respect to the tangent line to the rotational path of the crushing edge at the contact position.

If the pulp sheet is guided to the contact position along the tangent line to the rotational path of the crushing edge at the contact position, a force toward the cutter is not acting on the pulp sheet. Thus, the pulp sheet may not be sufficiently crushed by the cutter.

Contrary to this, by guiding the pulp sheet to the contact position in the posture inclined with respect to the tangent line to the rotational path of the crushing edge at the contact position by the guiding section as in the above mode, the pulp sheet can be pulled toward the cutter by causing the force toward the cutter to act on the pulp sheet. This realizes more reliable crushing of the pulp sheet by the cutter.

In the above crusher, preferably, the axis horizontally extends and the contact position is located higher than a vertical center of the cutter.

Specifically, if the contact position is located lower than the vertical center of the cutter, pulp fibers produced by crushing the pulp sheet at the contact position fall down below the cutter by their own weights. Thus, these crushed pieces may not be sufficiently conveyed toward the downstream side in the rotational direction of the cutter.

Contrary to this, by locating the contact position higher than the vertical center of the cutter as in the above mode, the produced pulp fibers can be more reliably conveyed toward the downstream side in the rotational direction of the cutter according to the rotation of the cutter.

In the above crusher, the guiding section preferably guides the pulp sheet in a horizontal direction.

According to this mode, a moving speed of the pulp sheet into the inside of the casing is not affected by the own weight of the pulp sheet. Specifically, the moving speed of the pulp sheet is determined by the rotational force of the cutter or the driving force of the separately provided device for feeding the pulp sheet from the outside into the inside of the casing 5. Thus, this moving speed of the pulp sheet is easily managed.

Further, the present invention provides an absorber-manufacturing device for manufacturing an absorber, the absorber-manufacturing device including the above crusher, a fiber stacking machine configured to mold pulp fibers crushed by the crusher into a predetermined shape of the absorber and a duct configured to introduce the pulp fibers from the crusher to the fiber stacking machine.

Further, the present invention provides a pulp sheet-crushing method for crushing a pulp sheet using a crusher with a cutter configured to rotate about a predetermined axis and a casing configured to house the cutter, a crushing edge configured to crush the pulp sheet by coming into contact with the pulp sheet being provided on an outer periphery of the cutter, and a guiding section configured to guide the pulp sheet toward a contact position, where the pulp sheet and the crushing edge of the cutter come into contact, from outside of the casing into inside of the casing being provided in the casing, the pulp sheet-crushing method including a step of supplying the pulp sheet into the crusher through the guiding section such that the pulp sheet moves toward the contact position from a position upstream of a virtual line orthogonal to a tangent line to a rotational path of the crushing edge at the contact position and passing through the contact position in a rotational direction.

The invention claimed is:

1. A crusher for crushing a pulp sheet, comprising:
a cutter configured to rotate about a predetermined horizontal axis, the cutter having an outer periphery with a crushing edge configured to crush the pulp sheet by coming into contact with the pulp sheet; and
a casing configured to house the cutter,
the casing includes:
a peripheral wall covering the outer periphery of the cutter and extending in an arc shape along a rotational path of the crushing edge toward a downstream side in a rotational direction of the cutter from a position below the axis in a vertical direction to a position on the downstream side of a position above the axis in the vertical direction in the rotational direction of the cutter,
an outlet port for guiding pulp fibers crushed by the crushing edges to the outside of the casing, the outlet port being at a position between an upstream end and a downstream end of the peripheral wall in the rotational direction of the cutter; and
a guiding section configured to guide the pulp sheet toward a contact position, where the pulp sheet and the crushing edge of the cutter come into contact, from outside of the casing into inside of the casing, the guiding section including a through hole formed on the peripheral wall, the guiding section being provided entirely above a vertical center of the cutter in a position of the peripheral wall opposite to the outlet port with respect to a vertical surface passing through the axis of the cutter, such that the contact position is provided above a vertical center of the cutter, having a shape extending in the horizontal direction, and further guiding the whole pulp sheet in the horizontal direction to the contact position in a posture inclined with respect to a tangent line to the rotational path of the crushing edge at the contact position and
the guiding section guiding the pulp sheet toward the contact position from a position upstream of a virtual line orthogonal to the tangent line to the rotational path of the crushing edge at the contact position and passing through the contact position in a rotational direction.

2. A crusher according to claim 1, wherein the guiding section guides the pulp sheet to the contact position in a posture inclined with respect to the tangent line to the rotational path of the crushing edge at the contact position.

3. A crusher according to claim 1, wherein:
the axis horizontally extends; and
the contact position is located higher than a vertical center of the cutter.

4. A crusher according to claim 1, wherein the guiding section guides the pulp sheet in a horizontal direction.

5. An absorber-manufacturing device for manufacturing an absorber, comprising:
a crusher according to claim 1;
a fiber stacking machine configured to mold pulp fibers crushed by the crusher into a predetermined shape of the absorber; and
a duct configured to introduce the pulp fibers from the crusher to the fiber stacking machine.

6. The crusher according to claim 1, wherein:
the pulp sheet is pulled into the inside of the casing from the outside of the casing only by a rotational force of the cutter.

* * * * *